United States Patent [19]

Zwyssig

[11] 4,362,059
[45] Dec. 7, 1982

[54] ULTRASONIC TESTING METHOD AND APPARATUS

[75] Inventor: Jules Zwyssig, Schaffhausen, Switzerland

[73] Assignee: Georg Fischer Aktiengesellschaft, Switzerland

[21] Appl. No.: 253,907

[22] Filed: Apr. 14, 1981

[30] Foreign Application Priority Data

Apr. 16, 1980 [CH] Switzerland ........................ 2942/80

[51] Int. Cl.³ ............................................. G01N 29/04
[52] U.S. Cl. ........................................ 73/628; 73/641
[58] Field of Search ................ 73/598, 600, 625, 627, 73/628, 629, 633, 641, 624

[56] References Cited

U.S. PATENT DOCUMENTS

| | | | |
|---|---|---|---|
| 3,442,119 | 5/1969 | Cowan | 73/639 |
| 3,683,680 | 8/1972 | Johnson et al. | 73/628 |
| 3,768,306 | 10/1973 | Stearns | 73/625 |
| 3,924,454 | 12/1975 | McElroy et al. | 73/628 |
| 4,165,648 | 8/1979 | Pagano | 73/625 |

FOREIGN PATENT DOCUMENTS

| | | |
|---|---|---|
| 2006110 | 8/1972 | Fed. Rep. of Germany . |
| 2740106 | 3/1979 | Fed. Rep. of Germany ........ 73/628 |

*Primary Examiner*—Stephen A. Kreitman
*Attorney, Agent, or Firm*—Roylance, Abrams, Berdo & Farley

[57] ABSTRACT

An ultrasonic testing method permits investigating the nodal point in the profile of a cast wheel of a motor vehicle between clinch and wheel flange. Hollow spaces occurring in this area may be tolerated when the remaining wall thicknesses between the profile legs do not drop below a certain thickness. In order to be able to check a wheel in one single measuring process and with a simple measuring geometry, two of the three intermediate leg parts are tested by direct testing by an evaluation of the echo height in consequence of lateral contraction of ultrasonic energy or in consequence of partial reflection which allows one to make conclusions with regard to the cross section and sound spots of the material through which ultrasound was sent, while the remaining part is measured by means of a simple travel time transversely to the residual wall. An apparatus for performing this method is disclosed.

11 Claims, 7 Drawing Figures

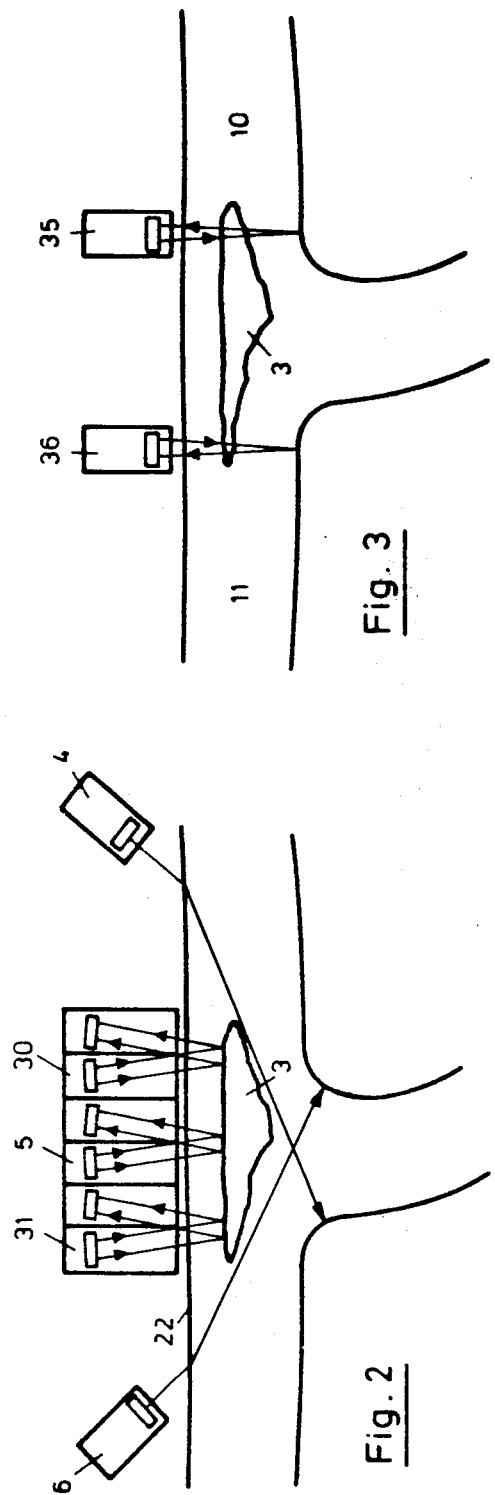

4,362,059

ULTRASONIC TESTING METHOD AND APPARATUS

This invention relates to an ultrasonic testing process for testing cast parts having flaws therein, as well as to an apparatus for carrying out the process.

BACKGROUND OF THE INVENTION

It is well known to test work pieces of various kinds by means of ultrasonic waves to locate unsound spots, or flaws, in the otherwise homogeneous structure. Depending upon the type of material and its form, methods were developed in order to test by means of an echo signal or an emitted ultrasonic impulse which is received by a transmitting-receiving transducer or, after emission from a pure transmitter, by a receiver. It is possible to use an arrangement wherein the transmitter is on one side of the work piece and the receiver on the other side, in which case an expert in this field speaks of a transmission technique wherein the intensity of the received ultrasonic energy is a measure of the perfection. On the other hand, when one uses an arrangement wherein the transmitter and receiver are both disposed on the same side of the work piece, then one speaks of an echo process wherein the temporal distribution of returning sound waves reflected from interfaces in the material is exploited.

In German Offenlegungsschrift No. 24 50 402, for example, a testing system employing the pulse-echo process and operating with several frequencies is disclosed. That system uses a testing head and several pulse transmitters by which signals of several frequencies can be produced which penetrate into different zones of the material in order to be able to deduce the location of faults in the cross section under test.

The thickness and the surface configuration of a wall which is inaccessible on one side can be measured by a process, for example, such as that shown in German No. OS 27 40 106 wherein the orientation of the rear wall can be determined by optimization of the receiving angle.

Another method for localizing faults is shown in German OS No. 20 06 110, according to which deductions can be made determining the location of a fault by setting an adjustable delay for one or two quasi stereo signals.

Finally, German Auslegeschrift No. 15 73 409 shows a carriage which carries test heads for the ultrasonic testing of railroad rails, the carriage being guided along the rails with the heads in order to carry out a continuous testing procedure.

All of these processes have the disadvantage that, although one can determine the location of a flaw, it is not possible to determine the form or shape of the flaw, or projecting portions thereof unless the work piece is scanned from several sides in accordance with known methods employing ultrasonics, in order to reconstruct the shape of, for example, a hollow space from a large number of detailed data.

BRIEF DESCRIPTION OF THE INVENTION

Accordingly, an object of the invention is to provide a method for testing a work piece with as few test heads as possible in such a way that the remaining wall thicknesses of parts containing flaws can be recognized as sufficient or as insufficient in circumstances wherein this is not possible by direct reflector proof on different parts because of inaccessibility or unfavorable geometry.

Briefly described, the invention includes a method of testing a cast part of the type having a junction region of T- or Y-shaped cross section wherein the part can have an inclusion flaw within the junction region for determining the remaining wall thicknesses between the flaw and the respective outer surfaces, comprising the steps of providing at least one first transducer coupled to the outer surface of the part at the top of the T or Y junction for transmitting ultrasonic energy generally in the direction of the leg of the T or Y; transmitting pulses of energy into the part from the first transducer, receiving energy resulting therefrom as a measure of thickness of the part between the top outer surface and the flaw; providing at least one second transducer coupled to the top outer surface of the part for transmitting ultrasonic energy in a direction forming a predetermined acute angle relative to the direction of transmission of the first transducer; locating the second transducer at a position spaced from the first transducer and transmitting pulses or energy into the part so that at least a portion of the energy passes between the flaw and the junction surface at the back surface of the part; receiving energy resulting therefrom as a measure of the spacing of the limits of the flaw from the back surface; and comparing the energy transmission thus determined with a standard to evaluate the remaining thicknesses.

In another aspect, the invention includes an apparatus for testing a cast part of the type having a junction region formed by three legs meeting at a T or Y shaped nodal point and wherein the part can have a cavity flaw in the junction region, for determining the distance from the flaw to the outer top and back surfaces of the part, the apparatus comprising a carriage; a first transducer mounted on said carriage and coupled to a surface of the part formed by two legs thereof for transmitting pulses of ultrasonic energy into the part in a direction substantially aligned with the third leg; second and third transducers mounted on said carriage and spaced from said first transducer on opposite sides of the plane containing said third leg, said second and third transducer being coupled to said surface of said part at angles for transmission of ultrasonic energy into the junction area between the flaw and the back surface corners formed by the junction of said first and second legs with said third leg; and means for determining the energy reflected and transmitted by said junction region and the flaw therein as a measure of remaining thickness.

The radial wall thickness to the acoustic irradiation surface is measured by one or several customary dual element, contact type standard test heads.

By additional monitoring of the form echo from the transition in the radius to the base of the rim or the outside surface of the dish to the inside-lying horn of the rim by at least two angular test heads, as well as by combining the signals with those of the remaining test heads, an evaluation of the position of the flaw is possible and of the extent, both in the cross section of the rim as well as in the direction of the periphery.

In order that the manner in which the foregoing and other objects are attained in accordance with the invention can be understood in detail, particularly advantageous embodiments thereof will be described in reference to the accompanying drawings, which form a part of the specification and wherein:

FIG. 1a is a radial section through a wheel for a motor vehicle, illustrating the testing geometry in the area of the nodal point;

FIG. 1b is a partial, enlarged, radial sectional view of a portion of FIG. 1a;

FIG. 2 is an enlarged view similar to FIG. 1b showing a further embodiment of the invention;

FIG. 3 is a view similar to FIG. 2 showing an arrangement of additional test heads to determine the extent of shrinkage cavities into legs of the wheel structure;

FIG. 4 is a view similar to FIG. 3 showing a modification of the test head arrangement;

Figures 1A, 1B:
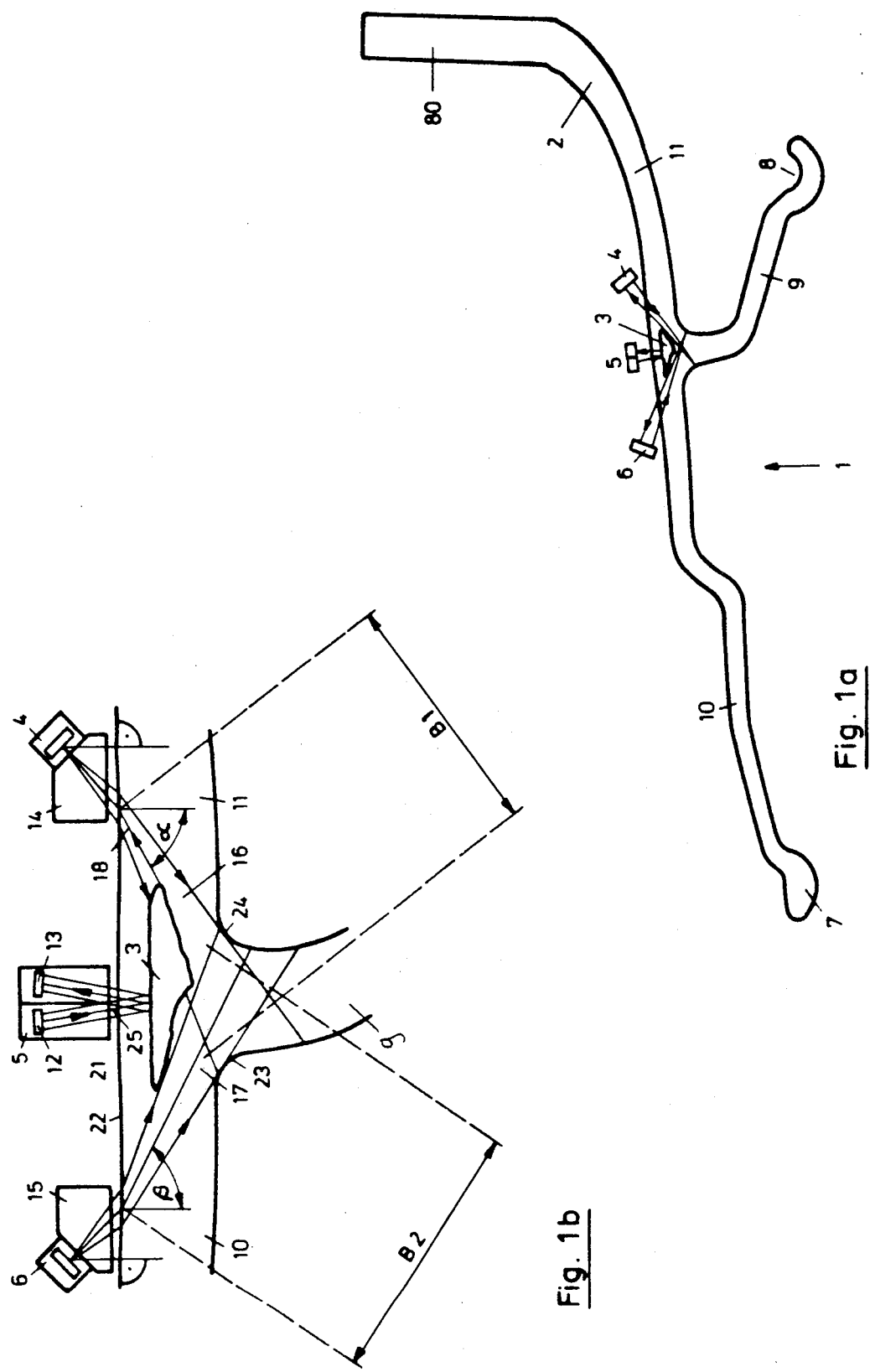

In FIG. 1a the radial section or profile of a wheel for a motor vehicle is shown, the wheel consisting of three main components including the clinch 1, the wheel dish 2 and the flange 80. The clinch 1 has two legs 9 and 10 which, at their ends, merge into the inside rim horn 7 and the outside rim horn 8. The horn 7 is full, the horn 8 carries on its inside a groove which serves for the reception of the balancing weights.

The rim bed 1 merges into the leg 11 forming the dish 2 which connects the clinch with the wheel flange 80. The dish 2 is normally penetrated by handling or inspection holes.

Because of new knowledge and processes in metallurgy, it is possible today to cast motor vehicle wheels in one piece. However, it frequently occurs during casting that inclusions or hollow spaces 3 develop within the material of the wheel and it is quite often the case that these spaces occur in the area of the nodal point formed at the junction of the three legs 9, 10 and 11. When these hollow spaces form in such a way that the wall thickness between the outer surface of the wheel and the wall of the cavity is below a minimum, the flaw can influence the strength of the connection of the clinch 1 with the dish 2 of the wheel. The residual wall thickness remaining as a result of this cavity 3 is measured by means of ultrasonics and at the same time the structure is tested for its soundness.

It should be noted that it is in no way necessary to demand absolute freedom from shrinkage cavities in this area. Rather, it is quite sufficient to simply be sure that the shortest distance from the hollow space to one surface of the profile does not drop below a predetermined thickness.

In order to have an arrangement for simple and quick testing, it is of great advantage to dispose all of the measuring heads on the same approximate area of the wheel and, moreover, to choose a location which is easily accessible. Such a location is shown in FIG. 1a. This same nodal point is shown in FIG. 1b somewhat enlarged for clearer illustration, the components in FIG. 1b having the same reference numerals as in FIG. 1a.

The testing apparatus includes a testing head 5 including a transmitter 12 and a receiver 13 which measures the thickness of the wall between the transducer and the closest surface of the cavity 3 in a conventional manner. The testing is accomplished employing immersion techniques. The thickness of the wall remaining between surface 22 and the closest interior surface of cavity 3 is determined from the travel time of the ultrasonic energy from surface 22 to the space 3 and back, multiplied by the speed of sound in the material. In this case, the thickness of a water film between the transducer and surface 22 is inconsequential because, after subtraction of the period of time between the transmitting impulse and the reflection from surface 22, it drops out of the time period between the reflection from surface 22 and the reflection from hollow space 3. The amount remaining is twice the travel time through the residual wall.

The two testing heads 4 and 6 operate according to a different principal and will be discussed in the following paragraphs. The apparatus includes wedges 14 and 15 which determine precise angles of incidence $\alpha$ and $\beta$, the heads 4 and 6 being mounted on the inclined surfaces of those wedges to transmit their bundles of energy 16 and 17 into the areas between the cavity 3 and rear wall of the cast piece.

With this arrangement, the energy waves 16 pass in between the cavity 3 and radius 24 and records by way of the head 4 by direct testing because of the narrowing of the sound energy through the hollow space 3 so that energy 18 is reflected by secondary hollow spaces or other reflectors located in the path of the energy within the testing area.

Energy bundle 17 travels in a similar manner, recognizing that the radii or the rear walls 23 and 24 are exchanged from reference to the bundle 16. The height of the total echo appearing depends upon the extent that the hollow space 3 projects into the included angle of the transmitted energy 16 or 17.

By using at least three testing heads, therefore, one can determine in a single operation whether or not the three residual wall thicknesses between the hollow space 3 and the surfaces 22, 23 and 24 are below the minimum values permitted.

The reference numbers B1 and B2 designate the testing areas of the energy bundles 16 or 17.

FIG. 2 illustrates, in section, the same nodal point as in FIG. 1b with the measuring heads, which are again identified by the same reference numerals 4, 5 and 6, operate in accordance with the same principals as have been described with reference to FIG. 1b.

In addition to the three testing heads 4, 5 and 6, in the embodiment of FIG. 2 there are two additional heads 30 and 31 which perform the same kind of measurement as head 5. This triplication of the measurement of the travel time serves for the purpose of obtaining information about the orientation of the limiting surface of cavity 3 on the testing side because, as will be recognized, the wall thickness remaining between cavity 3 and surface 22 is not necessarily uniform throughout. In the event that this surface has a slope with respect to surface 22, then the remaining wall thickness is less on one side and, with three heads, this minimum can be discovered.

In the embodiment shown in FIG. 3, two testing heads 35 and 36 are disposed in such a way that they transmit ultrasonic energy through the projections of legs 10 and 11 in order to test the extent of cavity 3 into those legs. The two heads shown in that figure is used in combination with the three or five heads shown, respectively, in FIGS. 1b and 2.

Yet another arrangement of these two additional heads, identified as 37 and 38, transmitting ultrasonic energy through the light projections is shown in FIG. 4.

Figure 5:
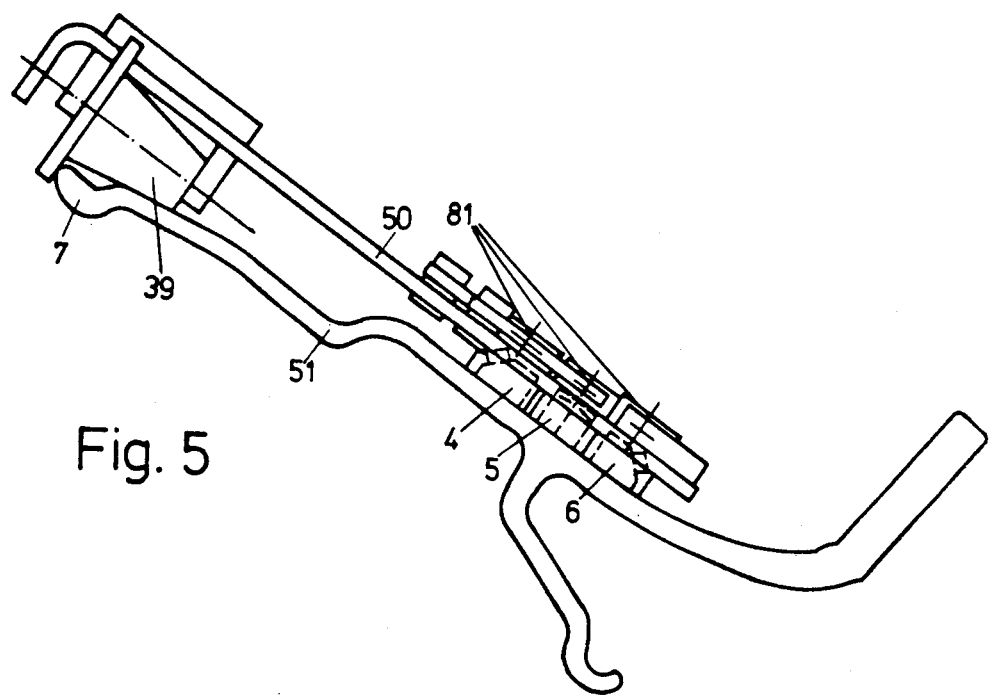
FIG. 5 is a radial sectional view showing test heads according to FIGS. 1a and 1b mounted on a test carriage.

FIG. 5 illustrates an arrangement favorable for sequential experiments with the five test heads 4, 5, 6, 35 and 36 (of which only 4, 5 and 6 are visible) on or under a carriage 50 which rolls on the profile 51 of the wheel. In order that the test heads can assume and maintain a constant and reproducible position with respect to profile 51, and especially relative to the nodal point, the carriage is provided with adjustable positioning mountings. The carriage 50 can be adjusted for different diameters and widths of the rims to be tested. The wheel 39 has a peripheral profile adapted to the horn 7 of the rim and thus guarantees that the carriage cannot slip to the right (as shown in the Figure) in the direction of the wheel flange during couterclockwise rotation thereof. The uniform distance of the test head relative to the acoustic irradiation surface is guaranteed either by supporting the test head with a support trailing on the surface of the casting or by a rolling support member near the test head.

The test heads 4, 5, 6 attached below carriage 50 are attached individually in supports mounted movably along axes 81 so that these heads can adapt themselves to the shape of the testing surface. Each test head support is adjustable relative to the test carriage and the nodal point on the basis of an aligning part corresponding to the type of wheel.

Figure 6:
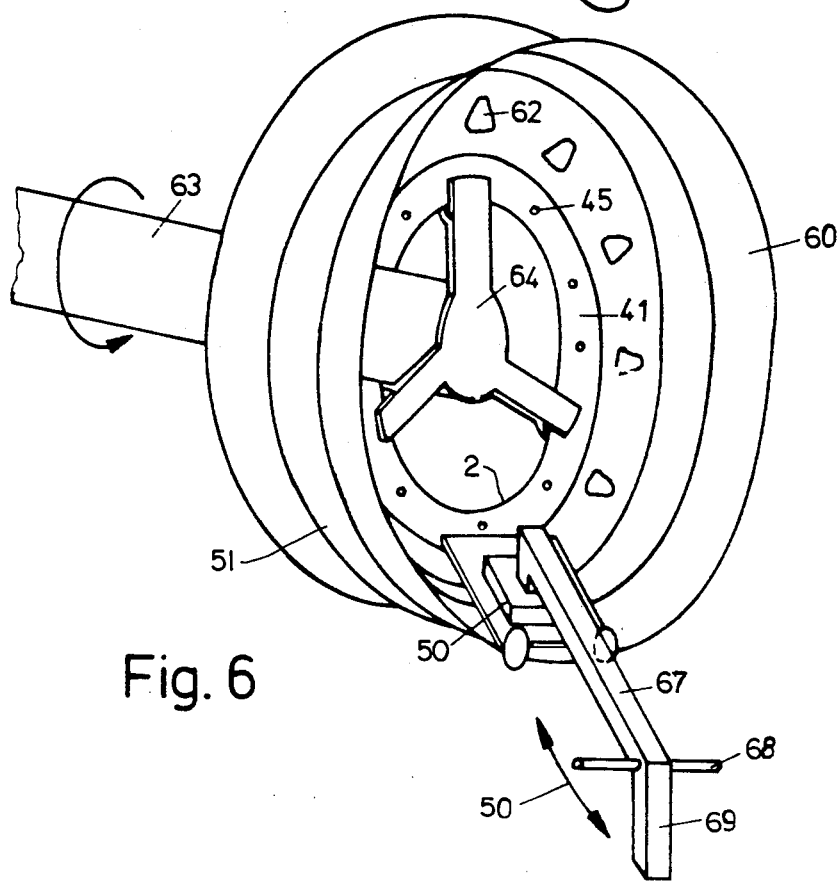
FIG. 6 is a perspective view showing the arrangement of a test carriage within a wheel at a testing station.

FIG. 6 shows the wheel 60 of a motor vehicle. The test carriage 50 is disposed adjacent the inside of the radius and, during testing, remains in place, being held either by a mechanical device or by hand, while the wheel 60 which is to be tested rotates past the testing head, being driven either mechanically or by hand. The test system of FIG. 5, stands in a water puddle, now shown, which provides fluid between the transducer and the work piece for perfect coupling of the ultrasonic energy.

As will be recognized, the process according to the invention is a relative process wherein, prior to testing, the heights of the signals and the points in time are calibrated by means of an aligning bore.

FIG. 6 shows a wheel 60 of a motor vehicle which is attached on a mounting star 64 rotatable by a driving shaft 63. The wheel includes the clinch 1 and the wheel flange 2 provided with screw holes 45, the bent part of which corresponding to the leg 11 of FIG. 1b, as several inspection holes 62 distributed over the periphery. The testing carriage 50 is disposed in the dish of the wheel, which, during the test, remains constant in its place and permits a smooth rotation past the wheel that is to be tested by means of its wheels 39 and 40 serving as a positioning device. The test carriage is attached to a toggle lever 67, 69 swivelable about the fix axis 68 which lever swings the test carriage 50 out of the wheel dish in the direction of the arrow 70 upon movement of the lever part 69 in order to permit a change of the wheel at the test stand.

While certain advantageous embodiments have been chosen to illustrate the invention it will be understood by those skilled in the art the various changes and modifications can be made therein without departing upon the scope of the invention as defined in the appended claims.

What is claimed is:

1. A method of testing a cast part of the type having a junction region of T- or Y-shaped cross section wherein the part can have an inclusion flaw within the junction region for determining the remaining wall thicknesses between the flaw and the respective outer surfaces, comprising the steps of
providing at least one first transducer coupled to the outer surface of the part at the top of the T or Y junction for transmitting ultrasonic energy generally in the direction of the leg of the T or Y;
transmitting pulses of energy into the part from the first transducer,
receiving energy resulting therefrom as a measure of thickness of the part between the top outer surface and the flaw;
providing at least one second transducer coupled to the top outer surface of the part for transmitting ultrasonic energy in a direction forming a predetermined acute angle relative to the direction of the first transducer;
locating the second transducer at a position spaced from the first transducer and transmitting pulses of energy into the part so that at least a portion of the energy passes between the flaw and the junction surface at the back surface of the part;
receiving energy resulting therefrom as a measure of the spacing of the limits of the flaw from the back surface; and
comparing the energy transmissions thus determined with a standard to evaluate the remaining thicknesses.

2. A method according to claim 1 wherein the thickness determined by the first transducer is determined by measuring the elapsed travel time of the ultrasonic energy;
and the thickness determined by the second transducer is determined by measuring the intensity of the energy passing through the space between the flaw and the back surface.

3. A method according to claim 1 or 2 wherein the junction region is formed by the intersection of three legs and the transducers are coupled to the surface between the two legs forming the largest angle.

4. A method according to claim 1 or 2 wherein a plurality of transducers are concurrently used for measurement over a larger test surface.

5. A method according to claim 1 or 2 wherein a plurality of transducers are used for measurement of the thickness between the outer, top surface and the flaw.

6. A method according to claim 1 or 2 wherein the part is a cast wheel for a motor vehicle.

7. An apparatus for testing a cast part of the type having a junction region formed by three legs meeting at a T or Y shaped point and wherein the part can have a cavity in the junction region, for determining the distances from the flaw to the outer top and back surfaces of the part, the apparatus comprising a carriage;
a first transducer mounted on said carriage and surface of the part formed by two legs thereof for transmitting pulses of ultrasonic energy into the part in a direction substantially aligned with the third leg;
second and third transducers mounted on said carriage and spaced from said first transducer or opposite sides of the plane containing said third leg,
said second and third transducers being coupled to said surface of said part at angles for transmission of ultrasonic energy into the junction area between the flaw and the back surface corners formed by the junction of said first and second legs with said third leg; and
means for determining the energy reflected and transmitted by said junction region and the flaw therein as a measure of remaining wall thickness.

8. An apparatus according to claim 7 wherein the part being tested is a vehicle wheel which is substantially symmetrical about its rotational axis, and wherein said carriage includes mounting means for adjusting the carriage position relative to said wheel.

9. An apparatus according to claim 8 wherein one of said wheel and carriage is movable relative to the other.

10. An apparatus according to claim 7 wherein said carriage is disposed in a fixed position relative to the axis of rotation of the wheel, and said wheel is rotatable about its axis.

11. An apparatus according to claim 7 or 10 wherein said carriage is disposed at a testing station whereby a succession of wheels can be positioned at said station, said carriage being pivotally mounted to be swung away from each tested wheel to permit positioning of the next wheel to be tested.

* * * * *